United States Patent [19]

Köhler et al.

[11] Patent Number: 5,045,573

[45] Date of Patent: Sep. 3, 1991

[54] PHOTOINITIATORS FOR PHOTOPOLYMERIZATION OF UNSATURATED SYSTEMS

[75] Inventors: Manfred Köhler, Darmstadt; Jörg Ohngemach, Ohngemach; Gregor Wehner, Darmstadt; Jürgen Gehlhaus, Lautertal, all of Fed. Rep. of Germany

[73] Assignee: Merck Patent Gesellschaft Mit Beschrankter Haftung, Darmstadt, Fed. Rep. of Germany

[21] Appl. No.: 337,773

[22] Filed: Apr. 13, 1989

Related U.S. Application Data

[62] Division of Ser. No. 948,305, Dec. 3, 1986, Pat. No. 4,861,916.

[30] Foreign Application Priority Data

Apr. 3, 1985 [DE] Fed. Rep. of Germany ....... 3512179

[51] Int. Cl.$^5$ ...................... C08F 2/50; C08F 220/06; C08F 226/02; C08G 59/17
[52] U.S. Cl. ........................................ 522/42; 522/39; 522/40; 522/43; 522/44; 522/46; 522/84; 522/96; 522/103; 522/14
[58] Field of Search ...................... 522/84, 39, 40, 42, 522/43, 44

[56] References Cited

U.S. PATENT DOCUMENTS 4,861,916 8/1989 Kohler et al. .......................... 522/40

Primary Examiner—Marion E. McCamish
Assistant Examiner—Arthur H. Koeckert
Attorney, Agent, or Firm—Millen, White & Zelano

[57] ABSTRACT

Compounds of the general formula I

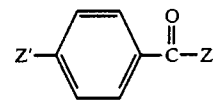

(I)

wherein
Z is $CR^1R^2(OR^3)$ or phenyl,
$R^1$ being H, $C_{1-6}$-alkyl or phenyl,
$R^2$ being H, $C_{1-6}$-alkyl or $C_{1-6}$-alkoxy and
$R^3$ being H, $C_{1-6}$-alkyl or $C_{1-6}$-alkanoyl and
Z' is $Y-[(CH_2)_m-X]_n-$,
X being $CH_2$ or 0,
Y being OH; COOH or $SO_3H$ including the alkali metal, alkaline earth metal or ammonium salts thereof and also the salts thereof with organic nitrogen bases; or NRR' in which R and R' are in each case H, $C_{1-20}$-alkyl or $C_{1-4}$-hydroxyalkyl, if appropriate quaternized or in the form of the acid addition salts, and
n and m each being the numbers 1-4, are excellently suitable as photoinitiators for the photopolymerization of ethylenically unsaturated compounds, in particular in aqueous systems.

7 Claims, No Drawings

PHOTOINITIATORS FOR PHOTOPOLYMERIZATION OF UNSATURATED SYSTEMS

This is a division of application Ser. No. 06/948,305 filed Dec. 3, 1986, now U.S. Pat. No. 4,861,916, National Phase of PCT/EP86/00183, filed Mar. 27, 1986.

The invention relates to new ketone derivatives and their use as photoinitiators for the photopolymerization of ethylenically unsaturated compounds or systems containing these.

The invention relates in particular to the use of these compounds as photoinitiators for the photopolymerization of ethylenically unsaturated compounds in aqueous systems and to aqueous photopolymerizable systems containing such ketone derivatives. The invention also relates to photopolymerization processes for the preparation of aqueous polymer solutions or polymer dispersions and for the preparation of water-soluble or hydrophilic polymers, in which processes ketones of this type are employed as photoinitiators. The invention furthermore relates to the use of these compounds as photoinitiators generally, that is to say also in non-aqueous systems, and corresponding photopolymerizable systems.

Photochemically induced polymerization reactions have acquired considerable importance in industry, particularly when the rapid curing of thin layers is involved, such as, for example, in the curing of lacquer and resin coatings on paper, metal and plastics or in the drying of printing inks, since these processes are distinguished, compared with conventional methods for printing and coating articles, by a saving in raw materials and energy and by reduced pollution of the environment.

The preparation of polymer materials in themselves by the polymerization of corresponding unsaturated monomeric starting materials is, however, also carried out photochemically in many cases. In addition to the customary processes of solution polymerization in organic solvents, solution polymerization and emulsion polymerization in aqueous systems are of importance in this connection.

Since, as a rule, none of the reactants in the said reactions is capable of absorbing the photochemically active radiation to an adequate extent, it is necessary to add so-called photoinitiators, which do not take part in the desired reaction, but are capable of absorbing irradiated light or UV radiation, transferring the energy thus absorbed to one of the reactants and thus forming active initiator radicals which, in turn, initiate the photopolymerization. Essential criteria for the selection of such initiators are, inter alia, the nature of the reactions to be carried out, the relationship of the absorption spectrum of the initiator to the spectral distribution of energy of the available source of radiation, the solubility of the initiator in the reaction mixture, the stability when stored in the dark of the reaction system to which the initiator has been added and the effect on the end products caused by residues remaining therein of the initiator and/or of the products formed therefrom during the photochemical reaction. In particular, the rate of the reaction depends greatly on the initiator used. There has, therefore, been no lack of attempts to find new initiators which exhibit increased reactivity in their power to initiate the photopolymerization of ethylenically unsaturated compounds or the curing of photopolymerizable systems.

The initiators which have hitherto been employed for the photopolymerization of unsaturated compounds are principally benzophenone derivatives, benzoin ethers, benzil ketals, dibenzosuberone derivatives, anthraquinones, xanthones, thioxanthones, α-halogenoacetophenone derivatives, dialkoxyacetophenones and hydroxyalkylphenones.

As is known, however, the industrial applicability of many of the substances mentioned is in some cases markedly limited by a number of disadvantages. These include, in particular, the fact that the reactivity in the power of initiating the photopolymerization of ethylenically unsaturated compounds is frequently too low. As well as molecule-specific reactivity, the solubility of the photoinitiators, or the capacity thereof to be incorporated as uniformly as possible, in the photopolymerizable systems frequently plays a decisive part in this respect.

For particular suitability for photopolymerization reactions in aqueous systems, this means that the photoinitiators must be adequately water-soluble within the concentration range customarily used and must, at the same time, be sufficiently reactive to ensure economically efficient utilization of the irradiation equipment. Economically efficient utilization in this context means not only the amount of energy required for complete conversion of monomeric material into polymer, which is reflected approximately in the lamp output to be made available and in the duration of irradiation, but in many cases also the degree of polymerization, attainable under the process conditions, of the polymer to be prepared, since many product properties and corresponding possible uses depend on this.

Photopolymerization reactions in aqueous systems by means of selected customary photoinitiators are known. For example, German Offenlegungsschrift 2,354,006 describes a process for the preparation of stable water-in-oil emulsions of water-soluble polymers, in which water-soluble monomers are introduced into a water-in-oil emulsion and are photopolymerized by the addition of at least one photoinitiator. German Offenlegungsschrift 2,831,263 describes the preparation of aqueous polymer solutions and polymer dispersions by photopolymerization, employing benzoin derivatives containing quaternary ammonium groups as the photoinitiators. The preparation of hydrophilic polymer materials by photochemical solution or emulsion polymerization in an aqueous medium is described in European Patent Applications 0,047,009 and 0,068,189, photoinitiators also being employed in this case.

The photoinitiators which have been disclosed in this connection do not, however, meet present-day requirements in respect of reactivity and solubility in water.

It was therefore required to find photoinitiators which have not only an excellent solubility in aqueous systems, but also a particularly high reactivity, in particular in respect of achieving particularly high molecular weights, or degrees of polymerization, in the polymers to be prepared.

It has now been found that these requirements are fulfilled in an excellent manner by ketone derivatives of the general formula I

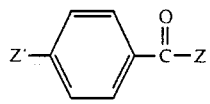

(1)

wherein
Z is $CR^1R^2(OR^3)$ or phenyl,
$R^1$ being H, $C_{1-6}$-alkyl or phenyl,
$R^2$ being H, $C_{1-6}$-alkyl or $C_{1-6}$-alkoxy and
$R^3$ being H, $C_{1-6}$-alkyl or $C_{1-6}$-alkanoyl and
Z' is $Y—[(CH_2)_m—X]_n—$,
X being $CH_2$ or O,
Y being OH; COOH or $SO_3H$ including the alkali metal, alkaline earth metal or ammonium salts thereof and also the salts thereof with organic nitrogen bases; or NRR' in which R and R' are in each case H, $C_{1-20}$-alkyl or $C_{1-4}$-hydroxyalkyl, if appropriate quaternized or in the form of the acid addition salts, and
n and m each being the numbers 1–4.

The compounds of the general formula I are highly effective photoinitiators and can be employed generally in photopolymerizable systems provided that the latter contain ethylenically unsaturated photopolymerizable compounds.

Because of the special substituent Z' on the phenyl ring of the phenone structural unit, the photoinitiators according to the invention furthermore have a pronounced hydrophylic or surfactant character which imparts to these compounds high water solubility and hence excellent properties in respect of uniform dispersibility in aqueous photopolymerizable systems. This is displayed to particular advantage both in systems in which the monomer material is present in aqueous solution and in systems in which the photopolymerizable components are dispersed in an aqueous medium.

The invention thus relates to the compounds of the general formula I.

The invention furthermore relates to the use of ketone derivatives of the general formula I as photoinitiators for the photopolymerization of ethylenically unsaturated compounds or systems containing these. The invention relates in particular to the use of the compounds of the formula I as photoinitiators in aqueous systems for example in the preparation of aqueous polymer solutions or polymer dispersions, or in the radiation-curing of coatings based on aqueous polymer dispersions.

The invention furthermore relates to aqueous and nonaqueous photopolymerizable systems containing at least one ethylenically unsaturated photopolymerizable compound, and, if appropriate, other known and customary additives, these systems containing at least one of the compounds of the formula I as photoinitiator, and processes for their photopolymerization.

The invention relates, in addition, to photopolymerization processes for the preparation of aqueous polymer solutions or polymer dispersions and for the preparation of water-soluble or hydrophilic polymers, the compounds of the formula I being employed as photoinitiators in these processes.

In regard to their radiation-reactive, active groups, the ketone derivatives according to the invention are structurally derived from known photoinitiator structures. In the general formula I, Z can be the grouping $—CR^1R^2(OR^3)$ or phenyl. In the first case this results in ketone derivatives of the sub-formula Ia

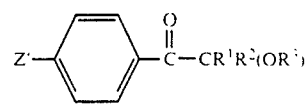

(Ia)

wherein Z', $R^1$, $R^2$ and $R^3$ have the meanings indicated above. If $R^1$ and $R^2$ are each hydrogen or alkyl and if $R^3$ is hydrogen, alkyl or alkanoyl, hydroxyalkylphenones, alkoxyalkylphenones and alkanoyloxyalkylphenones which are substituted by Z' result from sub-formula Ia, thus constituting derivatives of this class of photoinitiators which is by now very important. If $R^1$ is alkyl or phenyl and $R^2$ is alkoxy in sub-formula Ia, the corresponding compounds belong to the class of benzil ketals and dialkoxyacetophenones. If $R^1$ is phenyl and $R^2$ is hydrogen or alkyl, the corresponding compounds are benzoins or benzoin ether derivatives.

If, instead, Z in formula I is phenyl, ketone derivatives of the sub-formula Ib result

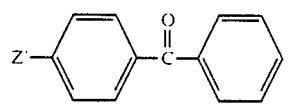

(Ib)

Corresponding derivatives are benzophenones substituted by Z'.

Preferred photoinitiators according to the invention are compounds according to sub-formula Ia, and of these in turn the corresponding hydroxyalkylphenone derivatives are particularly preferred. In these structures, $R^1$ and $R^2$ can be straight-chain or branched-chain alkyl having up to 6 C atoms. Preferred hydroxyalkylphenone derivatives are those in which $R^1$ and $R^2$ are methyl. Together, $R^1$ and $R^2$ can, however, also form a cycloalkane system. Compounds in which these radicals form a cyclohexane ring are also preferred.

In formula I Z' is the grouping $Y—[(CH_2)_m—X]_n—$. In this grouping X can be $CH_2$ or O; n and m are each the numbers 1–4.

If X is $CH_2$, this results in compounds in which the radical Y is attached via an alkylene bridge having 2–20 C atoms to the phenyl ring of the phenone structural unit, corresponding to sub-formula Ic

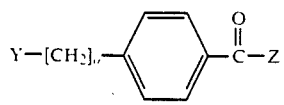

(Ic)

wherein o represents the numbers 2–20.

If X represents O, this results in compounds in which the radical Y is attached via 1–4 alkenyloxy groups to the phenyl ring, corresponding to sub-formula Id

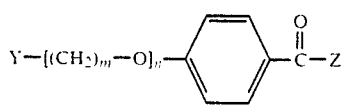

(Id)

Compounds according to formula Ic in which o is the numbers 2–5, and compounds according to formula Id in which n and m are each 1 or 2, are preferred.

Y is OH, COOH, $SO_3H$ and NRR'. Corresponding carboxylic or sulfonic acid derivatives can also be in the form of their alkali metal, alkaline earth metal or ammonium salts and also in the form of salts with organic nitrogen bases. The latter can be organic amines in which the amino nitrogen can carry one or more alkyl groups having up to 20 C atoms and/or hydroxyalkyl groups having up to 4 C atoms, or in which the nitrogen is part of a heterocyclic system. These amines can be, in particular, tertiary alkylamines or hydroxyalkylamines or pyridine, piperidine and morpholine derivatives. Salts with organic nitrogen bases which are particularly preferred are those in which these bases are organic amines which are known as coinitiators for photoinitiators or have the character of a surfactant. Examples of these are methyldiethanolamine, N-(2-hydroxyethyl)-morpholine, cetylamine and cetylpyridine.

In compounds in which Y is NRR', R and R' can each be hydrogen, alkyl having up to 20 C atoms or hydroxyalkyl having up to 4 C atoms. Amino derivatives of this type can, however, also be quaternized or can be in the form of their acid addition salts, such as, for example, their salts with hydrochloric acid, sulfuric acid or toluenesulfonic acid.

If the structural elements according to sub formulae Ia or Ib are combined in each case with those of the sub-formulae Ic or Id, in particular the relevant preferred structural variants, the preferred compounds of the general formula I are obtained.

These are, for example:
4-(2-hydroxyethyl)-phenyl 2-hydroxy-2-propyl ketone
4-(3-hydroxypropyl)-phenyl 2-hydroxy-2-propyl ketone
4-(2-aminoethyl)-phenyl 2-hydroxy-2-propyl ketone
4-(3-aminopropyl)-phenyl 2-hydroxy-2-propyl ketone
4-(2-hydroxycarbonylethyl)-phenyl 2-hydroxy-2-propyl ketone
4-(3-hydroxycarbonylpropyl)-phenyl 2-hydroxy-2-propyl ketone
4-(2-hydroxyethoxy)-phenyl 2-hydroxy-2-propyl ketone
4-(2-aminoethoxy)-phenyl 2-hydroxy-2-propyl ketone
4-[2-(hydroxymethoxy)-ethoxy]-phenyl 2-hydroxy-2-propyl ketone
4-(2-hydroxydiethoxy)-phenyl 2-hydroxy-2-propyl ketone
4-[2-(hydroxycarbonylmethoxy)-ethoxy]-phenyl 2-hydroxy-2propyl ketone
4-(2-hydroxyethyl)-benzophenone
4-(3-hydroxycarbonylpropyl)-benzophenone
4-(2-hydroxyethoxy)-benzophenone
4-(2-hydroxyethoxy)-diethoxyacetophenone The following compound is particularly preferred:
4-(2-hydroxyethoxy)-phenyl 2-hydroxy-2-propyl ketone.

The compounds of the general formula I can be prepared by standard processes of organic chemistry. The reaction conditions for these can be seen in the standard works of preparative organic chemistry, for example HOUBEN-WEYL, Methoden der organischen Chemie (Methods of Organic Chemistry), Georg-Thieme Verlag, Stuttgart or ORGANIC SYNTHESIS, J. Wiley, New York, London, Sydney.

Compounds of the general formula I can, for example, be obtained by carrying out a Friedel-Crafts acylation, using an appropriate carboxylic acid halide, on suitable phenyl derivatives which are substituted by Z' or by a grouping which is readily convertible into Z', in order to introduce the photoinitiator active structure or a precursor thereof.

Phenyl derivatives which are suitable as starting materials are, for instance, $\Omega$-phenylalkanols, such as 2phenylethanol, phenylalkanecarboxylic or phenoxyalkanecarboxylic acids, such as dihydrocinnamic acid or phenoxyacetic acid or a monoethoxylated or polyethoxylated phenol, such as 2-hydroxyethyl phenyl ether. It is advisable for the Friedel-Crafts acylation to protect the terminal functional groups by means of suitable protective groups which can later be removed, for instance by acylation in the case of the OH group or esterification in the case of the COOH group.

The photoinitiator active structure of the hydroxyalkylphenone type can be produced, for example, by acylation with an isobutyryl halide or an $\alpha$-chloroisobutyryl halide and subsequently introducing the hydroxy, alkoxy or alkanoyloxy grouping. Thus, for example, the Friedel-Crafts acylation of acylated 2-hydroxyethyl phenyl ether with isobutyryl chloride and subsequent bromination and saponification at the tertiary C atom gives the photoinitiator 4-(2-hydroxyethoxy)-phenyl 2-hydroxy-2-propyl ketone.

This compound can also be modified to give further photoinitiators of the formula I, for example by ethoxylation at the terminal OH group or by reaction with a bromoacetic ester and subsequent saponification, which gives the compound 4-[2-(hydroxycarbonylmethoxy)-ethoxy]phenyl 2-hydroxy-2-propyl ketone.

Replacement of the OH group by amino in accordance with the customary methods gives the corresponding amino derivatives, which can, if required, also be obtained in the form of their acid addition salts.

If the phenyl derivatives to be employed as the starting substances are acylated with, for example, a benzoyl halide, the corresponding benzophenone derivatives are immediately obtained.

Acylation with an acetyl halide or a phenylacetyl halide and subsequent oxidation gives acetoins or benzoins which can, in turn, be processed further to give the dialkoxyacetophenones, benzoin ethers and benzil ketals.

The compounds of the formula I can be employed as photoinitiators in a general manner in photopolymerizable systems, provided that ethylenically unsaturated photopolymerizable compounds are present in these systems. They are used in a manner which is completely analogous to that usually employed for known photoinitiators.

The addition to the photopolymerizable systems in the customary amounts of about 0.01-20% by weight, preferably 0.1-10% by weight, is carried out as a rule by simply dissolving and stirring in, since most of the photoinitiators to be used according to the invention are liquid or are at least readily soluble in the systems to be polymerized. A system to be polymerized is understood as meaning a mixture of free radical-initiated monofunctional or polyfunctional ethylenically unsaturated monomers, oligomers, prepolymers, polymers or mixtures of these oligomers, prepolymers and polymers with unsaturated monomers, which mixture, if necessary or desired, may contain further additives, such as, for example, antioxidants, light stabilizers, dyes or pigments, as well as other known photoinitiators and reaction accelerators.

Suitable unsaturated compounds are all those in which C=C double bonds are activated by, for example, halogen atoms or carbonyl, cyano, carboxyl, ester, amide, ether or aryl groups or by further conjugated double or triple bonds. Examples of such compounds are vinyl chloride, vinylidene chloride, acrylonitrile, methacrylonitrile, acrylamide, methacrylamide, methyl, ethyl, n- or tert-butyl, cyclohexyl, Z-ethylhexyl, benzyl, phenoxyethyl, hydroxyethyl, hydroxypropyl, lower alkoxyethyl or tetrahydrofurfuryl acrylate or methacrylate, vinyl acetate, propionate, acrylate or succinate, N-vinylpyrrolidone, N-vinylcarbazole, styrene, divinylbenzene, substituted styrenes and the mixtures of such unsaturated compounds.

The compounds according to the invention, of the formula I, are preferably used as photoinitiators in the UV-curing of thin layers, such as, for example, surface coatings on all conventional materials and substrates. These are mainly paper, wood, textile substrates, plastic and metal. Another important field of use is the drying or curing of surface coatings, printing inks and screen printing materials, the latter preferably being employed for coating, or producing designs on, the surface of, for example, cans, tubes and metallic closure caps.

According to the invention, the compounds according to the invention are outstandingly suitable, in particular, as photoinitiators for the photopolymerization of ethylenically unsaturated compounds in aqueous systems, owing to their pronounced hydrophylic character.

Aqueous systems are to be understood as meaning systems in which ethylenically unsaturated monomer materials are dissolved and/or emulsified in water. In this context, these systems can contain either only one specific monomer or mixtures of copolymerizable monomers of different types. Any ethylenically unsaturated compounds which are soluble in water to an adequate extent or which can be emulsified without problems in water are suitable. Primarily this relates to vinyl and acrylic compounds which have a high polarity as the result of appropriate functional groups. Examples of these are principally olefinically unsaturated monocarboxylic or dicarboxylic acids, such as, for example, acrylic acid, methacrylic acid, maleic acid and fumaric acid, the alkali metal and ammonium salts thereof, amides and nitriles of these acids, such as acrylamide, methacrylamide, maleimide, acrylonitrile or methacrylonitrile, or water-soluble vinyl compounds such as N-vinylpyrrolidone and N-vinylcarbazole. The photopolymerizable aqueous systems can contain 10-80% by weight, preferably 30-70% by weight, of these monomer materials.

In addition to the monomer materials mentioned, the radiation-curable systems can also contain further customary copolymerizable unsaturated compounds. These can be virtually any other monomers not hitherto mentioned, such as acrylic and methacrylic acid esters, vinyl derivatives, such as vinyl chloride, vinylidene chloride, styrene or divinylbenzene, or polyunsaturated compounds as crosslinking agents, such as, for instance, ethylene diacrylate, hexanediol diacrylate, trimethylol diacrylate or pentaerythritol triacrylate. It is also possible to add unsaturated oligomers, prepolymers or polymers such as, for instance, those based on acrylated polyester resins, epoxy resins and urethane resins. In aqueous systems, copolymerizable additives of this type are generally present in minor amounts compared with the water-soluble monomers and, as a rule, hardly exceed a proportion of 20% by weight of the total polymerizable material.

Furthermore, in the case of aqueous systems, it is also possible to add co-solvents, solubilizers or emulsifiers to the aqueous systems. Examples of these are aliphatic monoalcohols or polyalcohols, such as methanol, ethanol, isopropanol, glycol, glycerol, or anionic, cationic, amphoteric or non-ionic surfactants, such as sulfonated paraffin hydrocarbons, alkylsulfates, alkali metal salts of fatty acids, fatty alcohol sulfates, polyglycol ethers or ethoxylated alkylphenols. Additives of this type can be employed in the amounts which are generally customary.

The preparation of aqueous photopolymerizable systems is effected in a manner which is in itself customary, for instance by dissolving or homogeneously mixing the individual components, it being possible to employ the photoinitiators according to the invention in the concentrations customary for this purpose of 0.01 to about 20% by weight, relative to the content of polymerizable material. By virtue of their high activity and excellent solubility in water, the photoinitiators according to the invention can preferably be added to the aqueous photopolymerizable systems in an amount of 0.1-10% by weight, in particular 0.5-5% by weight, relative to the content of polymerizable material.

It is advantageous to employ reaction accelerators as well as the photoinitiators according to the invention in the photopolymerizable systems. Examples of reaction accelerators which can be added are organic amines, phosphines, alcohols and/or thiols all of which contain at least one CH group in the 1-position relative to the heteroatom. Examples of suitable accelerators are primary, secondary and tertiary aliphatic, aromatic, araliphatic or heterocyclic amines, such as, for instance, butylamine, dibutylamine, tributylamine, cyclohexylamine, benzyldimethylamine, dicyclohexylamine, triethanolamine, N-methyldiethanolamine, phenyldiethanolamine, piperidine, piperazine, morpholine, pyridine, quinoline, p-dimethylaminobenzoic acid esters, 4,4'-bis-dimethylaminobenzophenone (Michler's ketone) or 4,4'-bis-diethylaminobenzophenone. Tertiary amines, such as, for example, triethylamine, triisopropylamine, tributylamine, octyldimethylamine, dodecyldimethylamine, triethanolamine, N-methyldiethanolamine, N-butyldiethanolamine or tris-(hydroxypropyl)-amine, are particularly preferred.

These reaction accelerators, which are frequently also designated coinitiators, are also employed in the amounts customary for this purpose.

Aqueous photopolymerizable systems containing a tertiary organic amine as a reaction accelerator constitute a particularly preferred form of the present invention.

The photopolymerization can be initiated by the action of high-energy radiation, preferably UV light, on the photopolymerizable systems containing the photoinitiators according to the invention. The photopolymerization is effected in accordance with methods which are in themselves known by irradiation with light or UV radiation of the wavelength range 250–500 nm, preferably 300–400 um. Sunlight or artificial radiating elements can be used as sources of radiation. For example, mercury vapour high-pressure, medium-pressure or low-pressure lamps and also xenon and tungsten lamps are advantageous.

Photopolymerization using the photoinitiators according to the invention can be carried out either discontinuously or continuously. The duration of irradiation depends on how the photopolymerization is carried out, on the nature and concentration of the polymerizable materials employed, on the nature and amount of the photoinitiators used and on the intensity of the light source, and, in the case of mass polymerization, it can be within the range from a few seconds to minutes, depending on the size of the batch, but in the case of large batches can, for instance, also be in the range of hours.

The polymerization temperature can be selected as desired and can be +5 to approx. 100° C., it being preferable to carry out the photopolymerization at room temperature. The heat of polymerization which may be liberated can be removed by customary means of cooling.

Depending on the nature and content of polymerizable material in the aqueous photopolymerizable systems according to the invention, it is possible to obtain, by photopolymerization, aqueous polymer solutions or polymer dispersions containing between 10 and 80% by weight, usually between 30 and 70% by weight, of polymer material. By virtue of the high activity of the photoinitiators according to the invention, the conversion of monomer material into polymer material takes place virtually quantitatively. It is surprising in this respect that, compared with known photoinitiators, it is possible to obtain polymers having considerably higher average molecular weights by means of the photoinitiators according to the invention, under otherwise identical process conditions. Accordingly, the aqueous polymer solutions and polymer dispersions prepared by the process according to the invention can be employed in a diverse and broad range of applications. Thus, for example, the solution polymers are excellently suitable for use as flocculating agents for effluent purification, as auxiliaries in paper production and in the textile industry. The polymer dispersions are excellently suitable for coating paper, nonwovens and leather and can also be employed as base materials for paints and adhesives.

The polymer material can also be isolated by customary processes from the polymer solutions or dispersions prepared by the process according to the invention and can thus be made available in a pure form for a wide variety of applications. Thus, for example, high-molecular, partly crosslinked polymers based on acrylic acid are particularly suitable, by virtue of their hydrophilic character, as absorptive materials for water or aqueous electrolyte solutions, such as, for instance, body fluids. Polymer materials of this type have a high capacity and can often bind many times their own weight of liquids of this type. They can thus be used with particular advantage in the production of absorptive elements, for instance in hygiene and body care articles, such as, for example, napkins for babies. These polymers can be used in this respect in a loose or compact form or applied to suitable carrier materials, such as textile structures based on fabrics or nonwovens, or on paper products.

The examples which follow describe the preparation of the photoinitiators and their use in aqueous and nonaqueous systems and illustrate, in comparison with known photoinitiators, the advantageous properties of the former in photopolymerization in aqueous systems in regard to achieving a particularly high molecular weight in the polymer.

EXAMPLE 1

Preparation of 4-(2-hydroxyethoxy)-phenyl 2-hydroxy-2-propyl ketone a) 336 g (3.2 moles) of isobutyryl chloride are added dropwise, at −5° to 0° C., with stirring and in the course of 40 minutes, to 880 g (6.6 moles) of anhydrous aluminium chloride in 480 ml of methylene dichloride. 540 g (3.0 moles) of 2-phenoxyethyl acetate are then added dropwise at the same temperature in the course of 2 hours. When the dropwise addition is complete, the reaction mixture is stirred for a further 2 hours at the temperature indicated and is then poured into a mixture of 1.8 l of concentrated hydrochloric acid and 5 kg of ice. The organic phase is separated off, and the aqueous layer is extracted with methylene dichloride. The combined organic phases are washed with water, dried and concentrated, and the residue is distilled in vacuo.

This gives 740 g (98.7%) of 4-(2-acetoxyethoxy)-phenyl 2-propyl ketone, boiling point 145°–152° C./0.3–0.5 mm Hg.

b) 250 g (1.0 mole) of 4-(2-acetoxyethoxy)-phenyl 2-propyl ketone are dissolved in 200 ml of glacial acetic acid, and 192 g (1.2 moles) of bromine are added, with stirring, at 25° C. and in the course of 2 hours. Stirring is continued for approx. 10 hours and the mixture is then poured into 3 l of glacial acetic acid. The product is extracted with ethyl acetate. The combined extracts are dried, and concentrating the latter gives 365 g of a viscous oil. This is dissolved in 1 l of ethanol, and 380 g of 32% strength sodium hydroxide solution are added, with stirring, at 25° C. and in the course of 20 minutes. Stirring is continued for 10 minutes, and the ethanol is then removed. The oily residue is poured into 3 l of ice water, and this mixture is extracted several times with a total of 1.5 l of ethyl acetate. 250 g of oily crude product are isolated after drying, filtering and concentrating the solution. Recrystallization from acetone/petroleum ether and/or purification by chromatography gives 145 g (65%) of 4-(2-hydroxyethoxy)-phenyl 2-hydroxy-2-propyl ketone in the form of a colourless solid of melting point 88°–90° C.

EXAMPLE 2

4-(2-Hydroxyethyl)-phenyl 2-hydroxy-2-propyl ketone is obtained analogously to Example 1, but using 2-phenylethyl acetate as the starting substance.

EXAMPLE 3

4-(3-Hydroxypropyl)-phenyl 2-hydroxy-2-propyl ketone is obtained analogously, but using 3-phenylpropyl acetate as the starting substance.

EXAMPLE 4

4-(2-Hydroxycarbonylethyl)-phenyl 2-hydroxy-2-propyl ketone is obtained analogously, but using methyl 4-phenylpropionate as the starting substance.

EXAMPLE 5

4-(2-Hydroxycarbonylpropyl)-phenyl 2-hydroxy-2-propyl ketone of melting point 57° C. is obtained analogously, but using methyl 4-phenylbutyrate as the starting substance.

The corresponding sodium salt, melting point: 210°, is obtained by reacting the resulting acid with aqueous sodium carbonate solution.

The corresponding ammonium salt, melting point: 142°, is obtained by reaction with aqueous ammonium carbonate solution.

EXAMPLE 6

Preparation of 4-(2-hydroxyethoxy)-benzophenone:

a) 135 g (0.75 mole) of 2-phenoxyethyl acetate are added dropwise, at −5° C., with stirring and in the course of 40 minutes, to 240 g (1.8 moles) of anhydrous aluminium chloride in 1,200 ml of methylene dichloride. 110 g (0.78 mole) of benzoyl chloride are then added dropwise at the same temperature in the course 9f 2 hours. When the dropwise addition is complete, the reaction mixture is stirred for a further hour at the temperature indicated and is then poured into a mixture of 450 ml of concentrated hydrochloric acid and 570 g of ice.

The organic phase is separated off and the aqueous layer is extracted with methylene dichloride. The combined organic phases are washed with water, dried and concentrated, and the residue is distilled in vacuo. This gives 107 g (92%) of 4-(2-acetoxyethoxy)-benzophenone, boiling point 178°–182° C./0.25 mm Hg.

b) 43 g (0.15 mole) of 4-(2-acetoxyethoxy)-benzophenone are dissolved in 60 ml of ethanol and boiled with 17 ml of 32% strength sodium hydroxide solution under reflux, with stirring, for 20 minutes. After cooling, the reaction mixture is neutralized with hydrochloric acid, whereupon the end product is precipitated as a white solid. The reaction mixture is poured into 500 ml of water, and the solid is filtered off with suction, washed and dried in vacuo at 50° C. for 5 hours. This gives 35 g (95%) of 4-(2-hydroxyethoxy)-benzophenone, melting point 82° C.

EXAMPLE 7

4-(2-Hydroxyethyl)-benzophenone is obtained analogously to Example 6, but using 2-phenylethyl acetate as the starting substance.

EXAMPLE 8

4-(3-Hydroxycarbonylpropyl)-benzophenone is obtained analogously to Example 6, but using methyl 4-phenylbutyrate as the starting substance.

EXAMPLE 9

Radiation-curing of a nonaqueous coating.

5 parts by weight of 4-(2-hydroxyethoxy)-phenyl 2-hydroxy-2-propyl ketone (initiator according to Example 1) are added to a UV-curable binder system which consists of 75 parts by weight of an oligomeric epoxide acrylate (Laromer® LR 8555 from BASF) and 25 parts by weight of hexanediol diacrylate.

The ready-to-use formulation is applied onto degreased glass plates (10 × 10 cm) in a thickness of 50 μm, using coil coaters. Thereafter, the coatings are cured in an exposure apparatus ("Mini-Cure" apparatus from Primarc Ltd.) under a medium-pressure mercury lamp (lamp power 80 watt/cm) at a belt speed of 10 m/min. The exposure distance is about 10 cm.

Completely cured, non-tacky coatings are obtained.

Equally good results are obtained in an analogous manner, using the initiators of Examples 2-8.

EXAMPLE 10

Radiation-curing of a nonaqueous coating

A UV-curable binder system consisting of 60 parts by weight of an acrylated polyurethane prepolymer (Prepolymer VPS 1748 from Degussa AG), 40 parts by weight of hexanediol diacrylate, 15 parts by weight of pentaerythritol triacrylate and 5 parts by weight of 4-(2-hydroxyethyl)-phenyl 2-hydroxy-2-propyl ketone (initiator according to Example 2) is processed analogously to Example 6 to give 50 μm thick coatings, and the latter are cured at a belt speed of 30 m/min. Completely cured, non-tacky coatings are obtained.

The use of initiators according to Example 1 and 3-8 by a similar method gives equally good results.

EXAMPLE 11

UV-curable printing ink 63.5 parts of an epoxide acrylate resin (Laromer® 8555 from BASF, Ludwigshafen) are milled with 36.5 parts of butanediol diacrylate and 20 parts of Heliogen blue on a three-roll mill. 5 parts of 4-(2-hydroxyethyl)-phenyl 2-hydroxy-2-propyl ketone (initiator according to Example 2) are stirred into the suspension in the course of 10 minutes. The printing ink thus obtained is printed onto art paper in a 1 μm thick layer, and cured at a belt speed of 50 m/min and a radiant power of 160 W/cm. The printed sheets obtained are immediately stackable.

The photoinitiators stated in the Examples 1 and 3-8 can be used as UV curing agents for printing inks, analogously to Example 11.

EXAMPLE 12

UV-curable white enamel 63.5 parts by weight of a urethane acrylate resin (Uvimer® 530 from Bayer, Leverkusen) are milled with 36.5 parts by weight of butanediol diacrylate and 100 parts of titanium dioxide (anatase) in a porcelain ball mill. Thereafter, 5 parts by weight of 4-(2-hydroxyethoxy)phenyl 2-hydroxy-2-propyl ketone (initiator according to Example 1) and 3 parts by weight of N-methyldiethanolamine are stirred in. The coating, which is applied onto glass plates in a layer thickness of 10 μm, can be cured at a belt speed of 50 m/min and using a radiant power of 160 W/cm to give an odourless film which does not yellow.

The compounds stated in Examples 2 to 8 and 5 can be incorporated as photoinitiators into a pigmented coating, analogously to Example 12.

EXAMPLE 13

Radiation-curing of a coating based on an aqueous system 20 g of a dulling agent based on silica (dulling agent OK 412 from Degussa, Frankfurt/Main) are dispersed in 166 g of a 50% strength aqueous emulsion of an unsaturated acrylate resin (Laromer® LR 8576 from BASF AG, Ludwigshafen). After the dispersion has stood for 18 hours, a further 166 g of the 50% strength aqueous emulsion of the unsaturated acrylate resin and 35.2 g of water are added, with stirring, and 5 g of the compound 4-(2-hydroxyethoxy)-phenyl 2-hydroxy-2-propyl ketone (initiator according to Example 1) are stirred in.

The ready-to-use formulation is applied onto degreased glass plates (10 × 10 cm) in a thickness of 50 μm, using coil coaters. The coated glass plates are dried for 15 minutes at 100° C. Thereafter, the coatings are cured in an exposure apparatus ("Mini-Cure" apparatus from Primarc Ltd.) under a medium-pressure mercury lamp (lamp power 81 watt/cm) at a belt speed of 10 m/min. The exposure distance is about 10 cm.

Completely cured, non-tacky coatings are obtained.

Equally good results are obtained using the initiators of Examples 2-8 in an analogous manner.

EXAMPLE 14

Photopolymerization in an aqueous system (comparative tests).

A solution of

21% by weight of sodium acrylate,
9% by weight of acrylic acid and
70% by weight of water is prepared as a photopolymerizable aqueous system.

75 mg (0.5% by weight, relative to the amount of polymerizable compounds) of photoinitiator, together with 150 mg (1.0% by weight, relative to the amount of polymerizable compounds) of triethanolamine as coinitiator are stirred into 50 g portions of this solution. The photoinitiator used in this test is 4-(2-hydroxyethoxy)-phenyl 2-hydroxy-2-propyl ketone (initiator according to Example 1) and the known photoinitiators 1-phenyl-2-hydroxy-2-methylpropane-1-one (Darocur$^R$ 1173, made by E. Merck) and 4-(benzoylbenzyl)-trimethylammonium chloride (Quantacure$^R$ BTC, made by Ward Blenkinsop) are used for comparison. The first substance and the second of the two comparison substances dissolve completely in the aqueous system; the first of the comparison substances can only be dispersed to a varying extent.

The samples are poured into cells and the latter are each irradiated for exactly 30 seconds at a distance of 5 cm with an Hg lamp of 180 watts radiation output (type Q 600, made by Heraeus Original Hanau).

When the photopolymerization is complete, the polymer solutions are neutralized with aqueous sodium hydroxide solution, and the average molecular weights reached in the polymers are determined by viscosity measurement. These molecular weights provide information on the degree of polymerization achieved and thus on the effectiveness of the particular photoinitiator employed.

Table 1 below shows the results.

TABLE 1

| Photoinitiator | average molecular weight of polymer |
| --- | --- |
| 4-(2-Hydroxyethoxy)-phenyl 2-hydroxy-2-propyl ketone (compound according to the invention) | 1.4 · 10⁶ |
| 1-Phenyl-2-hydroxy-2-methylpropan-1-one (comparison substance) | 1.0 · 10⁶ |
| 4-(Benzoylbenzyl)-trimethylammonium chloride (comparison substance) | 0.23 · 10⁶ |

It is evident that considerably higher average molecular weights can be reached in the polymer using the photoinitiator according to the invention than using the known photoinitiators, under otherwise identical test conditions.

We claim:

1. A process for the photopolymerization of an ethylenically unsaturated compound or a system containing said compound, comprising exposing said compound or said system to activating radiation whereby polymerization is commenced, wherein said radiation is applied in the presence of a photoinitiator of formula I

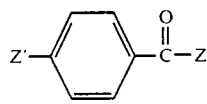

wherein
Z is CR$^1$R$^2$(OR$^3$),
R$^1$ being H, C$_{1-6}$-alkyl or phenyl,
R$^2$ being H, C$_{1-6}$-alkyl or C$_{1-6}$-alkoxy and
R$^3$ being H, C$_{1-6}$-alkyl or C$_{1-6}$-alkanoyl and
Z' is Y—[(CH$_2$)$_m$—X]$_n$—,
X being CH$_2$ or O,
Y being OH; COOH; SO$_3$H; an alkali metal, alkaline earth metal or ammonium salt thereof; a salt thereof with an organic nitrogen base; NRR' in which R and R' are in each case H, C$_{1-20}$-alkyl or C$_{1-4}$-hydroxyalkyl, or quaternized NRR' or NRR' in the form of an acid addition salt, and n and m each being a number 1–4.

2. A process according to claim 1, wherein the photoinitiator is
4-(2-hydroxyethyl)-phenyl 2-propyl ketone
4-(3-hydroxypropyl)-phenyl 2-hydroxy-2-propyl ketone
4-(2-aminoethyl)-phenyl 2-hydroxy-2-propyl ketone
4-(3-aminopropyl)-phenyl 2hydroxy-2-propyl ketone
4-(2-hydroxycarbonylethyl)-phenyl 2-hydroxy-2-propyl ketone
4-(3-hydroxycarbonylpropyl)-phenyl 2-hydroxy-2-propyl ketone
4-(2-hydroxyethyoxy)-phenyl 2-hydroxy-2-propyl ketone
4-(2-aminoethoxy)-phenyl 2-hydroxy-2-propyl ketone
4-[2-(hydroxymethoxy)-ethoxy]-phenyl 2-hydroxy-2-propyl ketone
4-(2-hydroxydiethoxy)-phenyl 2-hydroxy-2-propyl ketone or
4-[2-(hydroxycarbonylmethoxy)-ethoxy]-phenyl 2-hydroxy-2-propyl ketone.

3. A process according to claim 1, wherein the photoinitiator is 4-(2-hydroxyethoxy)-phenyl 2-hydroxy-2-propyl ketone.

4. A process according to claim 1, wherein the photoinitiator is added to the mixture to be polymerized before the photopolymerization is initiated.

5. A process according to claim 4, wherein 0.01 to 20% by weight of a compound of the formula I are added to the mixture to be polymerized before the photopolymerization is initiated.

6. A process for the preparation of an aqueous polymer solution or polymer dispersion comprising photopolymerizing of an ethylenically unsaturated compound present in an aqueous medium, wherein at least one compound of formula I

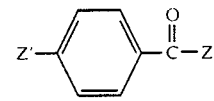

wherein
Z is CR$^1$R$^2$(OR$^3$),
R$^1$ being H, C$_{1-6}$-alkyl or phenyl,
R$^2$ being H, C$_{1-6}$-alkyl or C$_{1-6}$-alkoxy and
R$^3$ being H, C$_{1-6}$-alkyl or C$_{1-6}$-alkanoyl and
Z' is Y-[(CH$_2$)$_m$—X]$_n$—,
X being CH$_2$ or O,
Y being OH; COOH; SO$_3$H; an alkali metal, alkaline earth metal or ammonium salt thereof; a salt thereof with an organic nitrogen base; NRR' in which R and R' are in each case H, C$_{1-20}$alkyl or C$_{1-4}$-hydroxyalkyl, or quaternized NRR' or NRR' in the form of an acid addition salt, and n and m each being a number 1–4 is added, as a photoinitiator, to the mixture to be polymerized before the photopolymerization is initiated.

7. A process for the preparation of a water-soluble or hydrophilic polymer comprising photopolymerizing an ethylenically unsaturated compound present in an aqueous medium, wherein the photopolymerization is carried out in the presence of a photoinitiator of

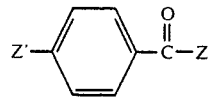

wherein

Z is $CR^1R^2(OR^3)$, $R^1$ being H, $C_{1-6}$-alkyl or phenyl, $R^2$ being H, $C_{1-6}$-alkyl or $C_{1-6}$-alkoxy and $R^3$ being H, $C_{1-6}$-alkyl or $C_{1-6}$-aklanoyl and Z' is $Y-[(CH_2)_m-X]_n-$, X being $CH_2$ or O, Y being OH; COOH; $SO_3H$; an alkali metal, alkaline earth metal or ammonium salt thereof; a salt thereof with an organic nitrogen base; NRR' in which R and R' are in each case H, $C_{1-20}$-alkyl or $C_{1-4}$-hydroxyalkyl, or quaternized NRR' or NRR' in the form of an acid addition salt, and n and m each being a number 1–4.

* * * * *